United States Patent [19]
Meade

[11] Patent Number: 5,499,998
[45] Date of Patent: Mar. 19, 1996

[54] ENDOSCOPTIC SURGICAL INSTRUMENT WITH GUIDED JAWS AND RATCHET CONTROL

[75] Inventor: John C. Meade, Walpole, Mass.

[73] Assignee: Microsurge, Inc., Needham, Mass.

[21] Appl. No.: 401,645

[22] Filed: Mar. 10, 1995

Related U.S. Application Data

[63] Continuation of Ser. No. 121,157, Sep. 14, 1993, abandoned.

[51] Int. Cl.$^6$ .................................................. A61B 17/00
[52] U.S. Cl. ............................ 606/207; 606/52; 606/208
[58] Field of Search ............................... 606/51, 52, 83, 606/127, 128, 170, 174, 205–211; 294/99.2; 128/751–755; 81/418

[56] References Cited

U.S. PATENT DOCUMENTS

| | | |
|---|---|---|
| 284,118 | 8/1883 | Cilley . |
| 2,060,366 | 10/1935 | Dunlap ..................................... 606/206 |
| 2,113,246 | 4/1938 | Wappler . |
| 4,712,545 | 12/1987 | Honkanen . |
| 4,976,723 | 12/1990 | Schad . |
| 5,009,661 | 4/1991 | Michelson . |
| 5,250,056 | 10/1993 | Hasson ..................................... 606/208 |
| 5,258,005 | 11/1993 | Christian ................................. 606/205 |
| 5,290,309 | 3/1994 | Kothe . |

FOREIGN PATENT DOCUMENTS

| | | |
|---|---|---|
| 0541930A1 | 5/1993 | European Pat. Off. . |
| 0543107A3 | 5/1993 | European Pat. Off. . |
| 3800331A1 | 7/1989 | Germany . |
| 3921935A1 | 2/1990 | Germany . |
| 9007356 | 5/1991 | Germany . |

*Primary Examiner*—Stephen C. Pellegrino
*Assistant Examiner*—William W. Lewis
*Attorney, Agent, or Firm*—Hamilton, Brook, Smith & Reynolds

[57] ABSTRACT

A surgical instrument comprising a handle assembly with a detachable tool assembly is disclosed. The tool assembly comprises rotatable jaws having arc defining portions near their proximal ends which define arcs having arc centers displaced from the jaws. The jaws are coupled to the distal end of an inner rod which is longitudinally translatable within an outer sleeve. When the inner rod is translated, a guide member at the distal end of the outer sleeve contacts the arc defining portion of the jaws such that each jaw rotates about the center of its arc. The handle assembly comprises a trigger which engages a translation member on the inner rod. As the trigger is rotated, the translation member carries the inner rod back and forth to actuate the jaws. The translation member is coupled to the inner rod via a coupler having a spring which limits the closing force applied to the jaws. The instrument also includes a ratchet feature function which allows closing force to be applied to the jaws in increments and also allows the jaws to be held in a closed position at a desired closing force.

34 Claims, 12 Drawing Sheets

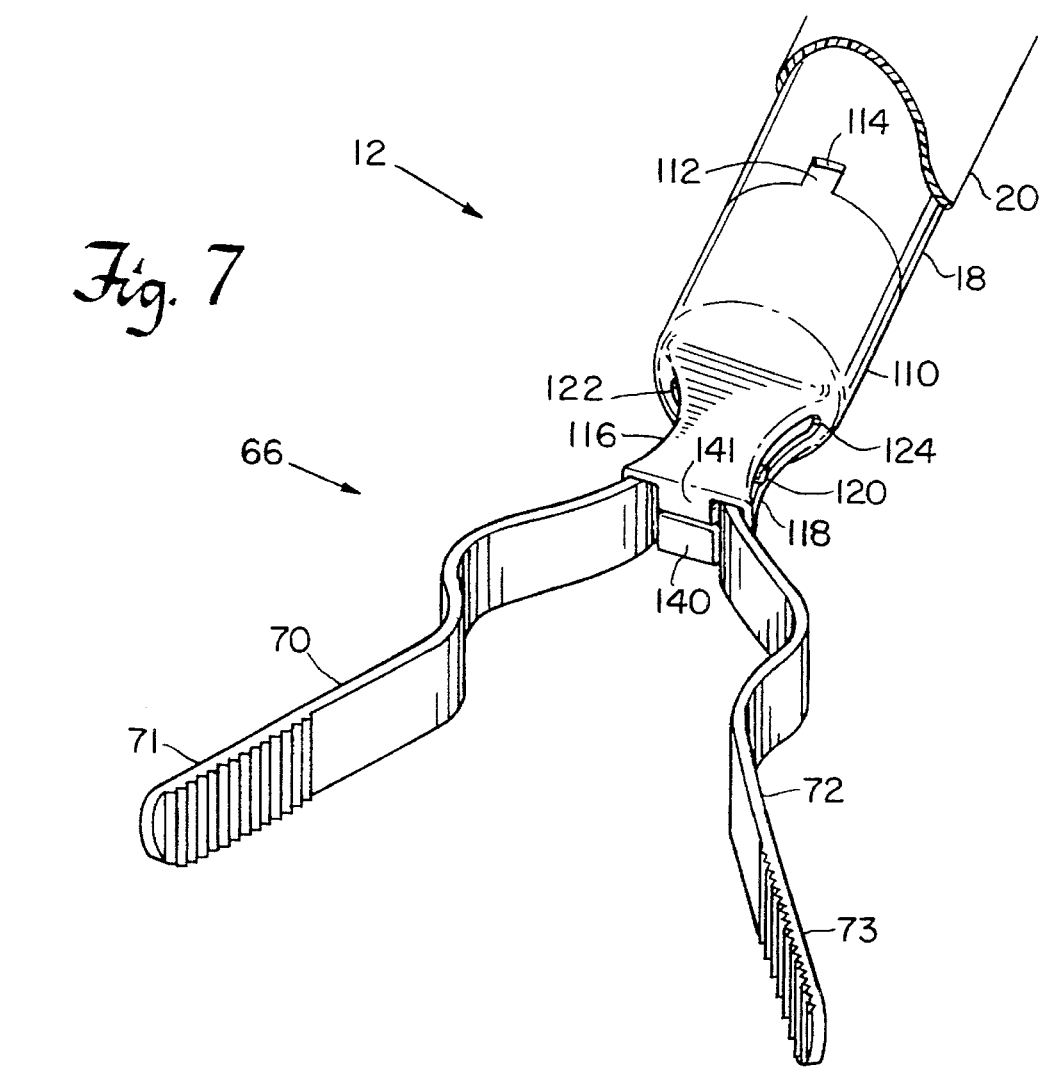
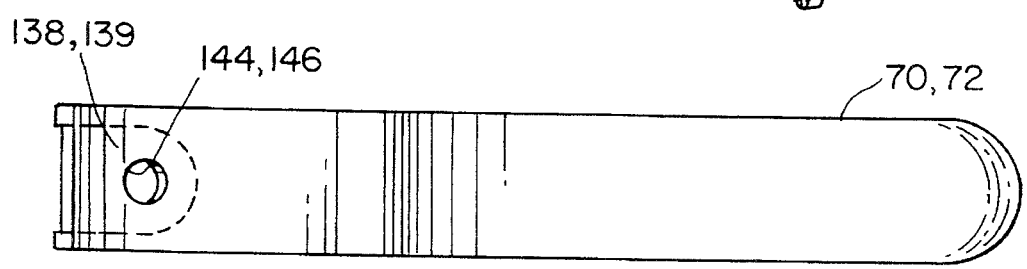
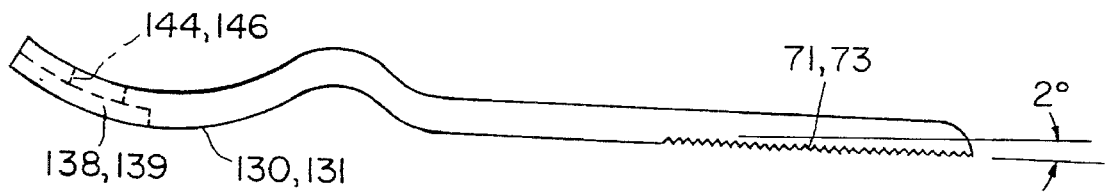

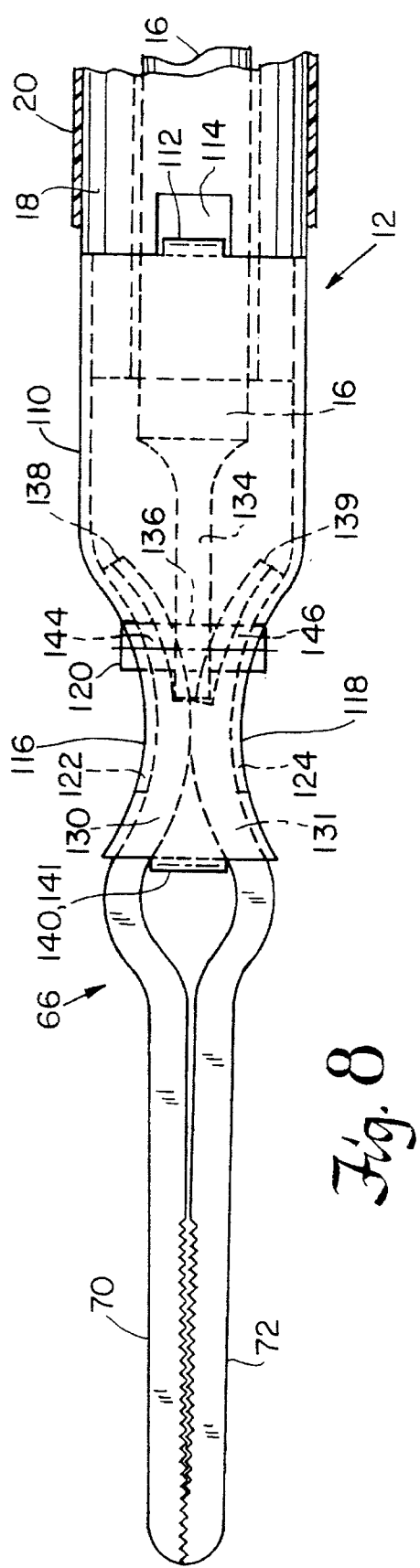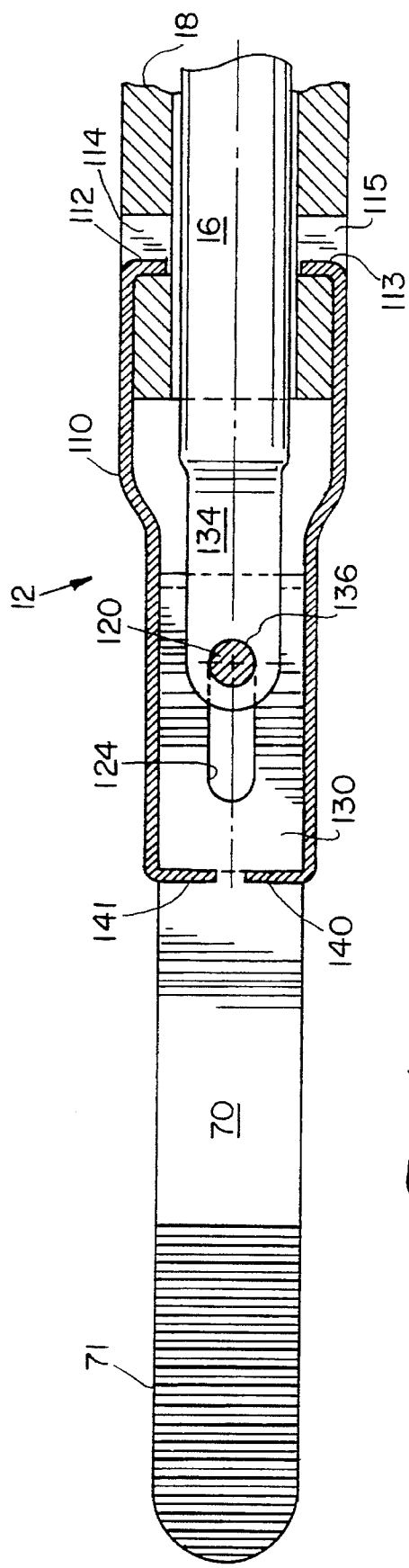
Fig. 8
Fig. 10

5,499,998

ENDOSCOPTIC SURGICAL INSTRUMENT WITH GUIDED JAWS AND RATCHET CONTROL

RELATED APPLICATION

This application is a continuation of application Ser. No. 08/121,157, filed on Sep. 14, 1993, now abandoned, which is incorporated herein by reference in its entirety.

BACKGROUND OF THE INVENTION

Since the late 1980s, endoscopic surgery has been growing in popularity at a very high rate. More and more, procedures which have customarily been performed by making large incisions in the patient's body are now being performed by "minimally invasive" or endoscopic methods. It has been estimated that by the year 2000, 40 to 50 percent of all surgeries will be done endoscopically.

Endoscope is the generic term for a viewing tube which can be inserted into the body. In endoscopic surgery, the surgeon makes a hole or portal in the patient's body with a sharp punch-like device called a trocar which is inserted through a sleeve or cannula. The trocar is then removed, leaving the cannula in the portal. The surgeon then inserts desired instruments into the body via the cannula. The instruments generally include a light source, a TV camera, and surgical tools such as scissors, graspers, dissectors and the like.

With the increase in endoscopic procedures has come an increase in demand for surgical instruments adapted for endoscopic applications. Specifically, the instruments must be small in cross-section to minimize trauma to the body. Also, they must be controllable from outside the body through an extended length. Precise control of instrument operation is imperative as any undesirable movement of the instrument during surgery can have disastrous results.

SUMMARY OF THE INVENTION

The present invention is directed to a surgical instrument which can be used in endoscopic applications. The surgical instrument comprises a tool assembly which is actuated by a handle assembly. The tool assembly includes an elongate jaw actuation device whose proximal end is retained within the handle and whose distal end is coupled to at least one rotatable jaw. The handle assembly actuates the jaw actuation device which in turn actuates the jaw to cause it to rotate.

The rotatable jaw includes a portion whose shape defines an arc having an arc center which is displaced from the jaw. This portion of the jaw may assume any shape which has a plurality of points which lie along the arc. In one embodiment, the portion itself is arcuate, but that need not be the case. Throughout this application, the portion of the jaw which defines the arc will be referred to as the arcuate portion, but, it will be understood that it need not actually have an arcuate shape.

The arcuate portion of the jaw is engaged by a guide member on the jaw actuation device. The jaw actuation device actuates the jaw by causing the jaw and the guide member to move relative to each other. The arcuate portion of the jaw slides along the guide member, causing the jaw to rotate approximately about the center of the arc. The tool assembly may have two rotatable jaws which rotate toward and away from each other as in the case of surgical graspers, scissors and the like. Each of the jaws has its own arcuate portion defining an arc center. Each of the arcuate portions slides along a guide member to cause its jaw to rotate about its own individual arc center.

In one embodiment, the jaw actuation device of the present invention comprises an inner rod within an outer sleeve. The jaw is coupled to the inner rod, and the guide member is coupled to the outer sleeve. The inner rod and outer sleeve are longitudinally translatable relative to each other. As the inner rod and outer sleeve are translated, the arcuate portion of the jaw slides along the guide member, and the jaw rotates. The handle assembly of the present invention retains the tool assembly and longitudinally translates the inner rod and outer sleeve relative to each other to cause the jaws to rotate.

In one embodiment, the guide member comprises an end cap attached to the distal end of the sleeve. The end cap has arcuate inner surfaces which engage the arcuate portions of the rotating jaws. The end cap also has spacing tabs which engage the jaws to maintain their arcuate portions in contact with the arcuate surfaces of the end cap as the inner rod and jaw translate relative to the outer sleeve and end cap.

The tool assembly can be retained by the handle assembly such that it is detachable and replaceable. This allows the user to select from a variety of tool assemblies to be actuated by the handle. It also allows for used tool assemblies to be discarded without discarding the reusable handle.

A translation member is coupled to the jaw actuation device. It is engageable by a tab on a rotatable trigger in the handle assembly. When the trigger is rotated, the tab translates the translation member back and forth. This translation motion is transmitted to the jaw actuation device to actuate the jaws.

The translation member is coupled to the jaw actuation device by a coupler. The coupler includes a spring which serves to limit the amount of closing force applied to the jaws. Thus, when the surgical instrument is a grasper, for example, the item being grasped is prevented from being crushed as the spring in the coupler absorbs the closing force. The spring also provides a sense of "feel" for the user.

The spring in the coupler can be selected based on the material to be grasped. For soft tissues, a small grasping force may be desired, and consequently, a spring with a small spring constant is used. For harder materials, a larger spring constant may be desired. Because the tool assemblies are detachable, the user can safely manipulate different tissues during an operation. A set of tool assemblies is available for use, each one having a different spring. If the type of tissue being manipulated changes, the user can change to an appropriate tool assembly.

In one embodiment, the translation member is coupled to the inner rod, and the outer sleeve is retained by the handle against longitudinal movement. As the trigger in the handle is rotated, translational motion is provided to the inner rod to rotate the jaw.

The surgical instrument of the present invention is also provided with a ratchet feature. When the ratchet feature is engaged, closing force can be applied to the jaws in increments. Also, the jaws can be held in a totally closed position or held clamped on an object at a desired closing force. A ratchet member having a row or rack of teeth or grooves couples the handle assembly to the tool assembly. As the translation motion is provided to the tool assembly, the row of grooves translates relative to a shoulder. As the translation continues, the shoulder engages and disengages each of the grooves in succession. If the motion stops, the engagement between the shoulder and one of the grooves will hold the tool assembly in its present position.

In one embodiment, the ratchet member is coupled to the handle assembly, and the shoulder is coupled to the tool assembly, preferably to the inner rod. As the inner rod is translated to rotate the jaws, it carries the shoulder along the grooves on the ratchet member.

The ratchet feature holds the jaws in the closed position via the engagement between the shoulder and a groove on the ratchet member. The ratchet member, the shoulder and the spring act together to allow the user to select an appropriate closing force for the jaws. When the jaws totally close or close on an object, the inner rod can no longer be translated. However, translation motion continues to be provided to the translation member against the compressing spring in the spring coupler. The further the translation member moves, the further the spring compresses, and thus, the greater the closing force applied to the jaw. When translation stops, the ratchet member holds the translation member stationary with a selected constant closing force applied to the jaws. Thus, the jaws can be closed on an object and locked in the closed position without crushing the object.

The ratchet member is controllably positionable between a first position in which the ratchet feature is engaged and a second position in which the ratchet feature is disengaged. In the first position, the grooves of the ratchet member engage the shoulder as the inner rod is translated. In the second position of the ratchet member, the grooves are prevented from engaging the shoulder, and the inner rod of the jaw actuation device can be translated back and forth to open and close the jaws freely. The spring coupler of the tool assembly provides the force limitation and feel features when the ratchet feature is engaged as well as when it is disengaged.

The surgical instrument of the present invention provides numerous advantages. Because the tool assembly is detachable, the handle assembly is reusable. Dull and used tools can be discarded and replaced with fresh ones. The entire instrument need not be replaced. This provides significant cost savings over devices which must be completely replaced.

Also, the detachability of the tool assembly allows the user to select from different tool assemblies to be used with the handle. As described above, the spring force of the spring coupler in the tool assembly is selected based upon the material intended to be grasped or cut by the jaws. It is contemplated that a specific tool assembly identified by its spring constant would be associated with specific tissue to be cut or grasped. Because the handle is detachable from the tool assembly, the user may obtain a set of tool assemblies and only one handle. The handle is attached to the appropriate tool assembly for the tissue to be cut or grasped. Again, this provides for significant cost savings because the user need not buy a handle for each individual tool assembly.

The ratchet feature also provides the surgical instrument with various advantages. The jaws of the instrument can be held closed in a desired position under a desired spring force without the user having to hold the instrument in position. The ratchet locks the jaws at the desired position. Thus, the ratchet feature allows the instrument to serve as a clamp with adjustable closing force.

The jaws of the present invention provide a stronger and smoother closing action than prior instruments. In other typical instruments, a jaw pivots about a pivot point which is common to both of the jaws. The jaws operate by a lever action in which closing the proximal ends of the jaws opens the distal ends, and vice versa. In contrast, each of the jaws of the present invention rotates individually about its own rotate point located at the center of the arc defined by the jaw. The center of the arc is displaced away from the jaw. Longitudinal translation is transformed into rotational motion as the arcuate portions of the jaws slide along the guide member such that each of the jaws rotates about the center of its own arc.

The rate of rotation achieved for a given rate of translation is determined by the radius of the arc. A small radius will provide a relatively large amount of rotation. A large radius will provide a smaller amount of rotation and thus a gradual, smooth closing action with greater closing force. Because the arc center of the jaws are displaced beyond the jaws, large arc radii, and thus high closing forces, can be obtained. The arc radius of the jaw of the present invention is preferably between approximately 0.180 inch and 0.250 inch. The sliding rotational motion of the present invention also provides a smoother jaw motion than the lever action of prior instruments.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 7 is a perspective view of the distal end of the tool assembly of the present invention with the jaws open.

FIG. 8 is a side elevational view of the distal end of the tool assembly of the present invention with the jaws closed.

FIG. 10 is a top cross-sectional view of the distal end of the tool assembly of the present invention.

FIG. 11a is a top view of a jaw in accordance with the present invention.

FIG. 11b is a side view of the jaw of FIG. 11a.

DETAILED DESCRIPTION OF THE INVENTION

Figure 1:
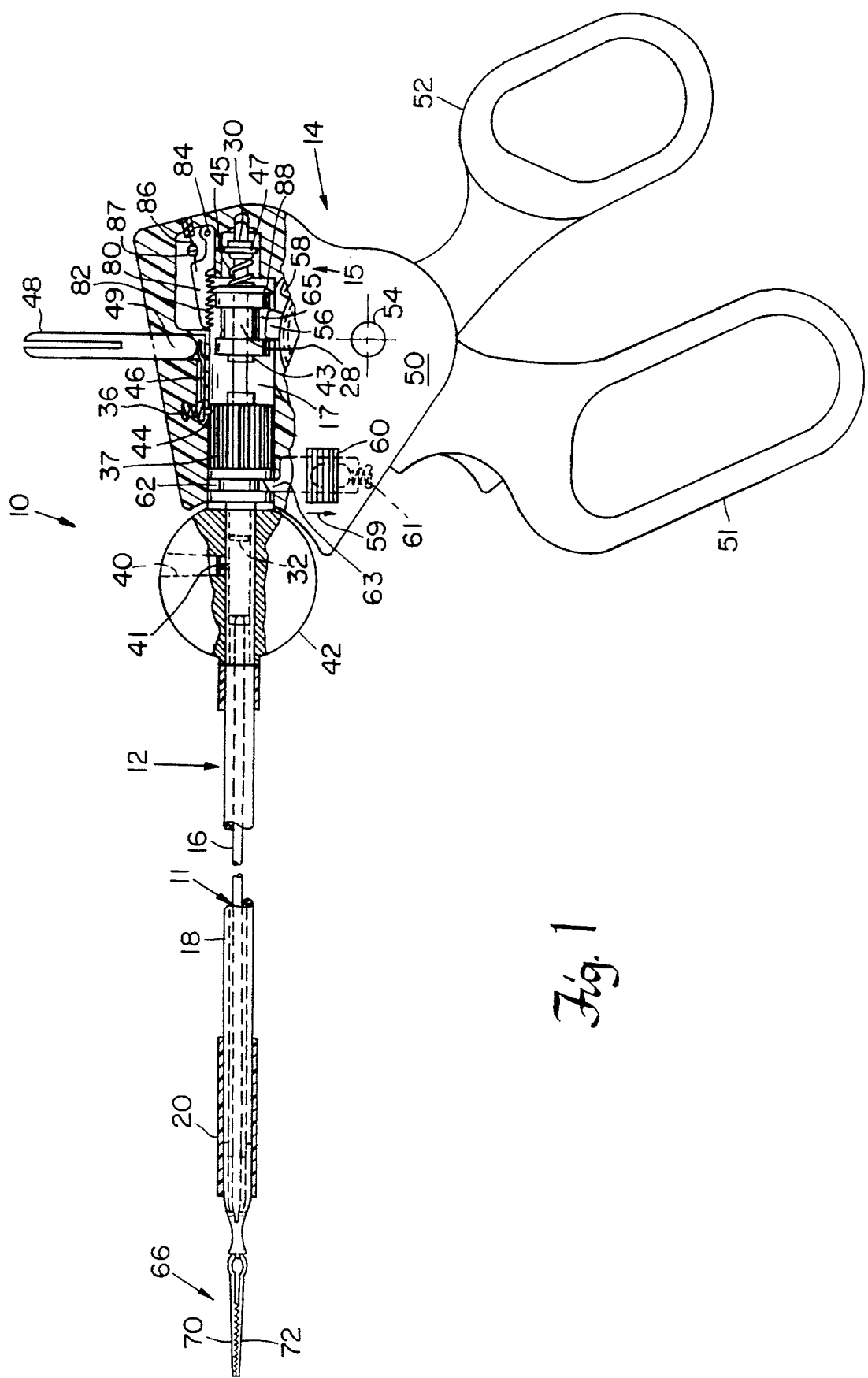
FIG. 1 is a partially cut-away side elevational view of the surgical instrument of the present invention.

FIG. 1 is a side elevational view of an embodiment of the surgical instrument 10 of the present invention. FIG. 1 depicts a tool assembly 12 retained in a handle assembly 14. The tool assembly 12 comprises a jaw actuation device 11 having an inner rod 16 located inside an outer sleeve 18. A non-conductive cover 20 covers the sleeve 18. A grasper type jaw assembly 66 is shown attached to the distal end of the jaw actuation device 11. The jaw assembly 66 comprises grasper jaws 70 and 72. It will be understood that although the following detailed description refers to a grasper device, the invention is applicable to other types of devices having rotatable jaws such as scissors, dissectors, clamps and the like.

The handle assembly 14 comprises a housing or base 50 having a port 17 in which the tool assembly 12 is retained. The handle assembly 14 also comprises a tool actuation trigger or thumb loop 52 pivotably mounted to the base 50 via pivot 54. The base 50 comprises a finger loop 51. During normal use of the instrument, the user places his fingers in the finger loop 51 to steady the base 50 and places his thumb through the thumb loop or actuation trigger 52. The actuation trigger 52 is rotated about pivot 54 to actuate the tool assembly.

The inner rod 16 is longitudinally translatable relative to the sleeve 18. As described in detail below, when the inner rod 16 is translated back toward the proximal end of the tool assembly 12, the jaw assembly 66 is actuated such that jaws 70 and 72 rotate toward the closed position shown. When the rod 16 is translated toward the distal end of the tool assembly 12, the jaws 70 and 72 open.

The rod 16 is sealed to the inside surface of the sleeve 18 by O-ring 32. This seal prevents body fluids and gases such as carbon dioxide from traveling to the proximal end of the tool assembly 12 during surgery. It also prevents cleaning fluids from traveling to the proximal end of the tool assembly 12 during a cleaning process to be described below.

The tool assembly 12 can be rotated about its longitudinal axis as a single unit within the handle 14. Rotating knob 42 is fixedly attached to the sleeve 18. To rotate the tool assembly 12, the user rotates the rotating knob 42. This imparts rotational motion to the sleeve 18. Because the rod 16 and sleeve 18 are coupled by the jaw assembly 66, the rod 16 also rotates. When the sleeve 18 and rod 16 are rotated, the jaw assembly 66 is also carried in the rotation.

The rotation of the tool assembly 12 is controlled such that the tool assembly 12 is rotated within certain indexed increments. This is accomplished by the index rotator 37, the spring 36, and the detent 44. The index rotator 37 is fixedly attached to the sleeve 18. The detent 44 is biased by spring 36 to engage the teeth on the outer surface of the index rotator 37. As the tool assembly 12 and the index rotator 37 are rotated, the detent 44 moves in and out of meshing engagement with the grooves on the index rotator 37. When a desired rotational angle is selected, the spring 36 provides sufficient force to the detent 44 to maintain the index rotator 37 and the tool assembly 12 stationary against inadvertent rotation.

The tool assembly 12 is retained within the port 17 of the handle 14 by engagement of the tapered end 63 of the spring-loaded retaining knob 60 with the retention groove 62 fixedly coupled to the outer sleeve 18. The retaining knob 60 is spring biased by spring 61 toward the engagement position. When the tool assembly 12 is inserted into the port 17, the end 63 of retaining knob 60 engages the retention groove 62 to retain the tool assembly 12 in place.

As described previously, actuation of the jaw assembly 66 is controlled by the longitudinal translation of the inner rod 16 within the outer sleeve 18. This longitudinal translation is controlled by the actuation trigger 52 of the handle 14. A translation member or spool 28 is coupled to the inner rod 16 by a coupler apparatus 15 comprising a retaining clip 43, a washer 47, a retaining clip 30 and a coil spring 45. The spool 28 is slidably mounted on the inner rod 16. It is retained against movement toward the distal end of the rod 16 by the stationary retaining clip 43. The coil spring 45 is retained against the proximal end of the spool 28 by the washer 47 and the stationary retaining clip 30. The spool 28 is thus slidable along the inner rod 16 toward the proximal end of the rod 16 against the spring force of the spring 45. If the spool 28 is translated proximally and the spring 45 does not compress, the inner rod 16 is carried with the spool 28 to actuate the jaw assembly 66 as described in detail below.

When the tool assembly 12 is installed in the port 17 of the handle 14, tab 56 on actuation trigger 52 meshes with translation groove 65 in the spool 28. As the actuation trigger 52 is rotated about pivot 54, the tab 56 moves within the port 17, carrying the spool 28 and the rod 16 with it. Thus, the angular motion of the actuation trigger 52 is translated into linear motion of the spool 28.

When the actuation trigger 52 is rotated in the clockwise direction, the spool 28 and the rod 16 are translated back toward the proximal end of the surgical instrument 10. As will be discussed below in detail, this proximal translation of the rod 16 with respect to the sleeve 18 causes the jaws 70 and 72 to move toward the closed position. If the jaws 70, 72 of the jaw assembly 66 have closed all the way or have closed on some object, proximal translation of the inner rod 16 will be impeded. If the impediment is sufficient, the spring 45 will compress as the actuation trigger 56 is rotated. Thus, the jaw closing force applied is limited by the spring 45.

The base 50 of the handle 14 also comprises a ratchet member 80 which is pivotably mounted to the base 50 by a pivot pin 84. The ratchet member 80 is pivotable about the pivot pin 84 against a flat spring 86 between an engagement position as shown in the figure and a disengagement position. Pivoting of the ratchet member 80 is controlled by a rotatable ratchet control member or axle 87. In the engagement position, a ratchet function of the instrument 10 is implemented. The teeth or grooves 82 on the ratchet member 80 engage the shoulder 88 on the spool 28. The grooves 82 and shoulder 88 are tapered such that as the shoulder 88 translates proximally, it passes in and out of engagement with the grooves 82 in succession. The grooves 82 and shoulder 88 are also properly shaped such that if a groove is engaged with the shoulder 88, the spool 28 and thus the inner rod 16 will be prevented from translating in the distal direction. Thus, the ratchet function allows the jaws 70 and 72 to be closed, but not opened. In this mode, the jaw assembly 66 acts as a clamp.

The ratchet member 80 is rotatable about pivot 84 from the engagement position shown in FIG. 1 to a second disengagement position in which the ratchet function is disengaged. In that position, the teeth 82 on the ratchet member 80 do not engage the shoulder 88 on the spool 28. When the actuation trigger 52 is rotated in the counter-clockwise direction, the rod 16 is able to translate forward toward the distal end of the surgical instrument 10. This distal translation of the rod 16 causes the jaws 70 and 72 to open.

The spring 86 biases the ratchet member 80 toward the disengagement position. A flat portion 93 of the rotatable axle 87 allows the ratchet member to open. When the axle 87 is rotated, a round portion 95 of the axle 87 engages the flat spring 86 to rotate the ratchet member 80 to the engagement position. The ratchet function will be discussed below in detail.

The surgical instrument 10 of the present invention also provides for the electrical connections required for cautery procedures. These electrical connections are effected via the electrical connection port 49 in the handle 14. The electrically conducting spring clip 46 is exposed to the interior of the port 49. The clip 46 runs distally toward the front of the handle to spring 36 and detent 44. The distal end of the spring clip 46 is squeezed between the spring 36 and the detent 44, thus making a connection to the index rotator 37. The spring clip 46, the detent 44, the index rotator 37, the sleeve 18, and the jaw assembly 66 are all electrically conducting. Therefore, an electrical connection is made from the electrical connection port 49 to the jaw assembly 66. When desired, an electrical connection can be made via an electrical connector 48 inserted into electrical connection port 49. The non-conductive cover 20 on the outside of the sleeve 18 serves to insulate the electrified sleeve 18 from tissue in the body. This allows the user to limit the cautery operation to a well-defined area of tissue.

The tool assembly 12 and the handle 14 are detachable. To remove a tool assembly 12 from the handle 14, the user slides the spring-loaded retaining knob 60 down in the direction shown by arrow 59. This causes the end 63 of the knob 60 to disengage the retention groove 62. Next, the user may grasp the rotating knob 42 and pull the tool assembly 12 distally out of the port 17. Alternatively, the user may, while holding knob 60 down, rotate the actuation trigger 52 as far as possible in the counter-clockwise direction. This will cause tab 56 to disengage translation groove 65 in spool 28. In addition, tab 58 will engage the shoulder 88 to urge the inner rod 16 and the tool assembly 12 out of the port 17. After the spool 28 clears the tabs 56 and 58, the user may simply slide the tool assembly 12 the rest of the way out of the port 17.

To install a tool assembly 12 into a handle 14, the user first rotates the actuation trigger 52 as far as possible in the counter-clockwise direction. This causes tab 58 to protrude into the port 17. Next, the user simply slides a tool assembly 12 into the port 17. Because the end 63 of the retaining knob 60 is tapered, the user need not slide the knob 60 out of the way to allow the tool assembly 12 to slide back into the port 17. The knob 60 will simply be moved out of the way by interfering portions of the tool assembly 12 until the retention groove 62 is engaged by the end 63 of the knob 60.

During installation of a tool assembly 12, the spool 28 slides back within the port 17. As it does, the shoulder 88 engages the tab 58 protruding into the port 17. The rearward motion of the shoulder 88 forces the tab 58 out of the way by forcing the actuation trigger 52 to rotate in the clockwise direction. As the spool 28 slides all the way back into the port 17, the rotation of the actuation trigger 52 causes the tab 56 to engage the translation groove 65 on the spool 28. When the end 63 of the knob 60 engages with the retention groove 62, the tool assembly 12 is retained within the handle 14 and is ready for use.

The tool assembly 12 can also be provided with a cleaning port 40 in the rotating knob 42. This port 40 allows for the introduction of cleaning fluid into the tool assembly 12. A syringe full of cleaning fluid (not shown) may be inserted into the port 40. The cleaning fluid is then introduced via the port 40 into the interior of the tool assembly 12 between the inner rod 16 and the inside surface of the sleeve 18. The cleaning port 40 includes a valve 41 which permits the cleaning fluid to enter the tool assembly and prevents fluids within the tool assembly from escaping.

Figure 2:
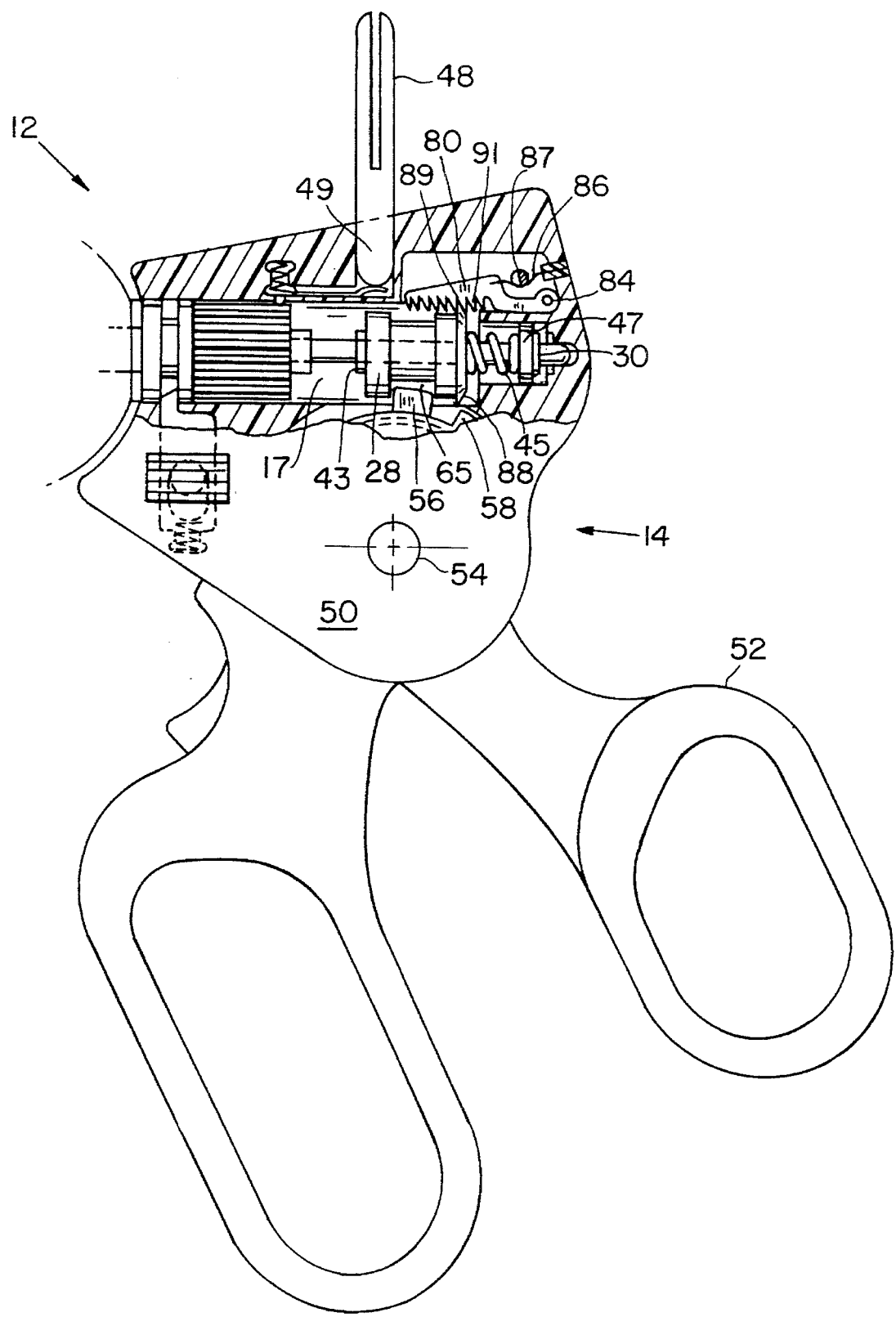
FIG. 2 is a partially cut-away side elevational view of the handle assembly of the present invention.

FIG. 2 is a partially cut-away elevational view of the handle assembly 14 of the present invention. The proximal end of the tool assembly 12 is shown retained within the port 17 of the handle assembly 14. The ratchet member 80 is shown pivoted to the engagement position by the axle 87 such that the ratchet function is implemented. A groove 89 on the ratchet member 80 is shown engaging the shoulder 88 on the inner rod 16. Because of the shape of the groove 89 and the shoulder 88, the spool 28 can only be translated toward the proximal end of the instrument 10. The shape of the groove 89 prevents the spool 28 and thus the inner rod 16 from being translated distally. Thus, the actuation trigger 52 will only rotate about pivot 54 in the clockwise direction. The ratchet function prevents the trigger 52 from rotating in the counter-clockwise direction.

If the jaws 70 and 72 of the jaw assembly 66 are closed all the way or have closed on an object as far as possible, the inner rod 16 cannot be translated further in the proximal direction. In this case, further clockwise rotation of the actuation trigger 52 will cause the spool 28 to slide in the proximal direction along the inner rod 16 while the inner rod 16 remains stationary. The spring 45 will compress as the spool 28 moves. The shoulder 88 will come out of engagement with groove 89 on ratchet member 80. Eventually, as the spool 28 continues to move, the shoulder 88 will slide into engagement with groove 91.

The ratchet member 80 is coupled to the housing or base 50 of the handle via the flat spring 86. One end of the spring 86 is mounted in the housing 50, and the other end is mounted in the ratchet member 80. As the spool 28 is translated proximately, the shoulder 88 comes in and out of engagement with the grooves or teeth 82 on the ratchet member 80. Specifically, as the spool slides back, the shoulder 88 will come out of engagement with groove 89. The tooth-like shape of the groove 89 and shoulder 88 forces the ratchet member 80 to pivot clockwise about pivot 84 against the spring force of spring 86. The shoulder 88 can be forced back far enough such that it comes out of engagement with groove 89 via the pivoting action of the ratchet member 80. If the spool 28 and shoulder 88 are translated further in the proximal direction, the groove 91 on the ratchet member 80 will snap into engagement with the shoulder 88 due to the spring force exerted toward the engagement position by the spring 86.

As described above, when the jaws 70 and 72 close all the way or close on an object, the inner rod 16 is no longer translatable in the proximal direction. However, the actuation trigger 52 is still rotatable to translate the spool 28 proximally. As the spool moves, the spring 45 compresses, thus applying more closing force through the inner rod 16 to the jaws 70 and 72. Thus, the spring 45 provides two functions. First, because the spool 28 is not directly coupled to the inner rod 16, the spring 45 serves to limit the closing force of the jaws to control the amount of force being applied to the object being grasped. In addition, after the jaws have closed on the object, the spring 45, in conjunction with the ratchet member 80, allows the user to apply an adjustable amount of closing force to the jaws. When the desired closing force is achieved, the ratchet member 80 holds the spool 28 in place. This keeps the jaws 70 and 72 closed on the object with the desired closing force. Thus, the surgical instrument 10 serves as a clamp.

Figure 3A:
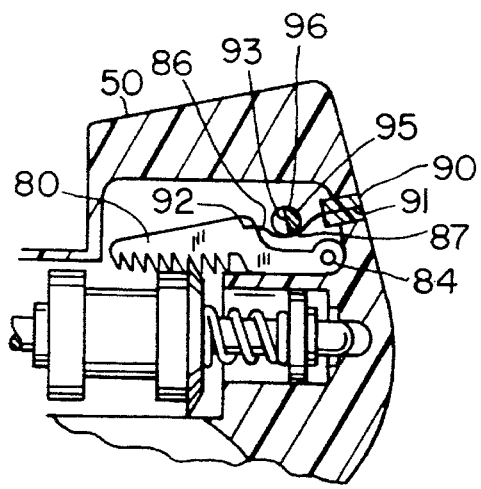
FIG. 3a is a partially cut-away side elevational view of a portion of the handle assembly with the ratchet feature engaged.
Figure 3B:
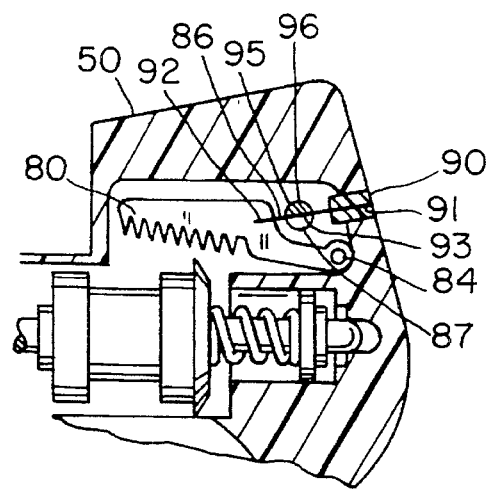
FIG. 3b is a partially cut-away side elevational view of the portion of the handle assembly of FIG. 3a with the ratchet feature disengaged.

As mentioned above, the ratchet member 80 is pivotable such that the ratchet function can be engaged and disengaged. The two positions of the ratchet member 80 are depicted in FIGS. 3a and 3b. FIG. 3a shows the ratchet member 80 with the ratchet function engaged. FIG. 3b shows the position of the ratchet member 80 when the ratchet function is disengaged. As previously described, the ratchet member 80 is pivotable about pivot 84 and is coupled to the housing 50 by spring 86. A first end 91 of the spring 86 is held in a molded clamp member 90 which is part of the housing 50. The other end 92 of the spring 86 is fixedly positioned in the ratchet member 80. The spring 86 rests across a rod portion 96 of the ratchet control member or axle 87. The axle 87 is rotatable about its center axis. As the axle 87 rotates, the rod portion 96 of the axle 87 engages the spring 86 to pivot the ratchet member 80 between the engagement and disengagement positions.

With the axle 87 in the orientation shown in FIG. 3b, the flat portion 93 of the rod 96 allows the spring 86 to maintain the ratchet member 80 in the disengagement position. In FIG. 3a, the axle 87 is shown rotated approximately 90° from the position shown in FIG. 3b. In the position shown in FIG. 3a, the spring 86 no longer rests on the flat side 93 of the rod 96 of the axle 87. The round portion 95 of the axle 87 engages the spring 86 to rotate the ratchet member 80 to the engagement position.

With the ratchet member 80 in the disengagement position shown in FIG. 3b, the surgical instrument 10 can be used as a grasper, dissector or scissor tool without a ratchet feature. The actuation trigger 52 can be rotated freely to open and close the jaws 70 and 72 of the jaw assembly 66. There is no engagement between a groove and the shoulder 88 to prevent distal translation of the inner rod 16. When the jaws 70 and 72 close down on an object, the spring 45 still limits the closing force applied and provides the user with an improved sense of feel. The only difference is that the ratchet member 80 no longer holds the jaws 70 and 72 in a desired closed position with a desired closing force. The user can alter the closing force by continuing to rotate the actuation trigger 52 after the jaws 70 and 72 have closed. However, when the actuation trigger 52 is released, the closing force will no longer be applied to the jaws.

As described above, when the surgical instrument is used with the ratchet feature engaged, it behaves like a clamp with an adjustable amount of closing force on the clamping members or jaws. When the desired closing force is set, the instrument 10 will maintain the jaws 70 and 72 closed without the user's intervention. In this mode of operation, the axle 87 serves as a release for the jaws 70 and 72. When it is desired to remove the instrument 10 from the clamped object, the axle 87 is rotated to the position shown in FIG. 3b. This allows the ratchet member 80 to pivot to the disengagement position. The shoulder 88 and the inner rod 16 are released and allowed to translate in the distal direction, thus releasing the jaws 70 and 72 and allowing them to open.

Figure 4:
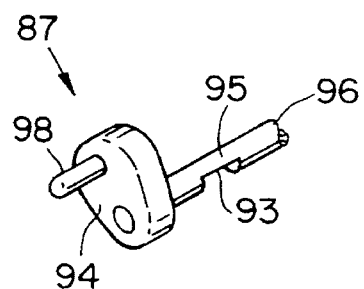
FIG. 4 is a perspective view of a ratchet control axle of the present invention.

FIG. 4 is a perspective view of the ratchet control member or axle 87. The axle 87 comprises a body 94, a handle 98, and an extended rod section 96 which has a flat side 93 and a round side 95 for engaging the spring 86 as described above. The user rotates the body 94 with the handle 98. The extended rod 96 rotates about its longitudinal axis such that the round portion 95 engages the spring 86 to pivot the ratchet member 80.

Figure 5:
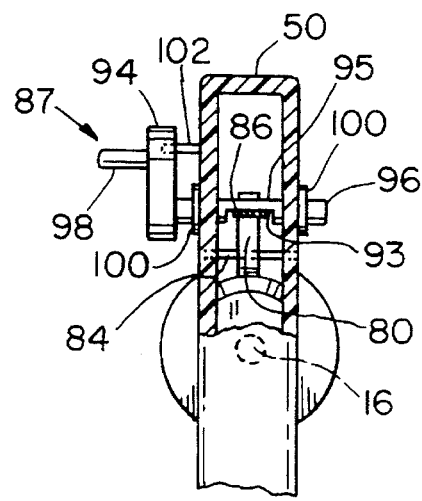
FIG. 5 is a partially cut-away view of the proximal end of the tool assembly showing the ratchet device of the present invention.

FIG. 5 is a partial cut-away view of the proximal end of the surgical instrument 10 looking in the distal direction. The figure shows the ratchet member 80 mounted to the housing 50 by the pivot pin 84 and the axle 87 mounted in the housing 50. The extended rod portion 96 of the axle 87 passes through the housing 50 as shown and is retained in place by retaining clips 100. A stop 102 is shown mounted to the housing 50. The stop limits the rotational movement of the axle 87. The instrument 10 is depicted with the ratchet feature disengaged. The spring 86 is shown resting against the flat section 93 of the rod 96.

Figure 6A:
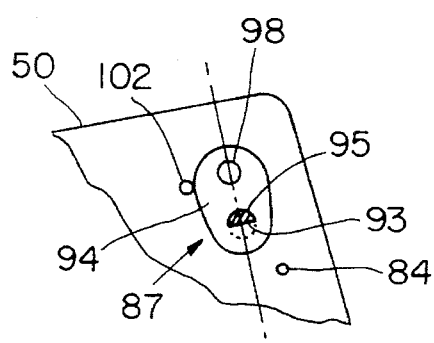
FIG. 6a is a schematic view of a portion of the handle assembly of the present invention showing the axle orientation with the ratchet feature engaged.
Figure 6B:
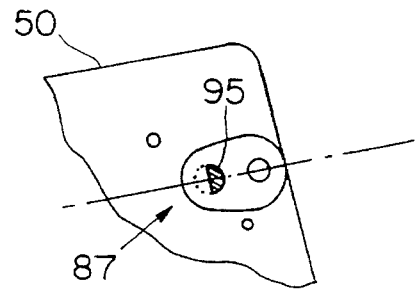
FIG. 6b is a schematic view of the portion of the handle assembly of FIG. 6a showing the axle orientation with the ratchet feature disengaged.

FIGS. 6a and 6b are schematic views showing the housing 50 and the rotational orientations of the axle 87 controlling the engagement and disengagement of the ratchet feature. FIG. 6a shows the orientation of the axle 87 when the ratchet feature is disengaged. FIG. 6b shows the orientation when the ratchet feature is engaged. The flat and round sections of the rod 96 are schematically depicted in the figures for purposes of illustration and clarity. In FIG. 6a, the rod 96 is oriented such that the spring 86 (not shown) will rest against the flat section 93, thus allowing the ratchet member 80 to pivot to the disengagement position. In FIG. 6b, the rod 96 is shown oriented such that the round portion 95 will engage the spring 86 to pivot the ratchet member 80 to the engagement position.

FIG. 7 is a perspective view of the distal end of the tool assembly 12 including the grasper jaw assembly 66. The jaw assembly 66 of the present invention will be described with reference to a surgical grasper. However, it will be understood that the inventive features are applicable equally as well to other surgical instruments comprising at least one rotatable jaw such as scissors and the like.

The grasper jaws 70 and 72 comprise blade portions 71 and 73, respectively, at their distal ends. The proximal ends of the jaws are retained within an end cap 110 attached to the sleeve 18. The jaws are separated from each other by spacing tabs 140 and 141 on the distal end of the end cap 110. The end cap 110 is attached to the sleeve 18 via a tab 112 bent into a hole 114 near the end of the sleeve 18 and a tab 113 in a hole 115 on the opposite side of the sleeve 18 not shown in the figure. It should be noted that the non-conductive cover 20 is shown cut away for clarity. In an actual instrument, the non-conductive cover 20 would extend distally over the end cap 110.

The end cap 110 comprises arcuate surface 116 and 118 which engage matching arcuate portions on the proximal ends of the jaws 70 and 72 (not shown). The spacing tabs 140 and 141 also engage the jaws 70 and 72 to keep their arcuate portions in contact with the arcuate surfaces 116 and 118. A drive pin 120 passes through holes in the proximal ends of the jaws 70 and 72. The pin 120 is translated back and forth along the slots 122 and 124 in the end cap 110. As it is translated, the jaws 70 and 72 are carried with it. The arcuate surfaces 116 and 118 and the spacing tabs 140 and 141 guide the arcuate portions of the jaws 70 and 72 to cause the jaws to rotate open and closed. The details of the actuation of the jaw assembly 66 as briefly outlined above will be described in detail below.

FIG. 8 is a side elevational view of the distal end of the tool assembly 12 of the present invention. The figure depicts the jaws 70 and 72 in a closed position. As shown in FIG. 8, the end cap 110 is attached to the distal end of the sleeve 18 by tab 112 on the end cap 110 bent into hole 114 in the sleeve 18. In similar fashion, on the opposite side of the sleeve 18, tab 113 is bent into a hole 115 in the sleeve 18 (see FIG. 10).

The proximal ends of the jaws 70 and 72 are retained within the distal end of the end cap 110. Arcuate portions 130 and 131 of the jaws 70 and 72, respectively, engage arcuate surfaces 116 and 118, respectively, of the end cap 110. The jaws are separated from each other by tabs 140 and 141 on the distal end of the end cap 110. The tabs 140 and 141 also maintain the arcuate portions 130 and 131 of the jaws 70 and 72 in contact with the arcuate inner surfaces 116 and 118 of the end cap 110. Thus, the spacing tabs 140 and 141 and the arcuate surfaces 116 and 118 serve as a guide member which guides the arcuate portions 130 and 131 as the jaws are translated such that the jaws 70 and 72 rotate about the centers of the arcs defined by their respective arcuate portions.

Drive pin 120 is retained within a hole 136 in the distal end 134 of the inner rod 16. The drive pin 120 also passes through hole 144 in jaw 70 and hole 146 in jaw 72. To actuate the jaw assembly 66, the inner rod 16 is made to longitudinally translate relative to the sleeve 18 and the end cap 110 as described in detail above. As the inner rod 16 moves, the drive pin 120 slides within slots 122 and 124 (shown more clearly in FIG. 10) and carries the jaws 70 and 72 with it. As the jaws move, the guiding arcuate surfaces 116 and 118 of the end cap 110 engage the arcuate portions 130 and 131 of the jaws 70, 72 to cause them to rotate.

In FIG. 8, the inner rod 16 is shown translated toward the proximal end of the tool assembly 12. This results in the jaws being in the closed position. If the inner rod 16 is translated distally, the drive pin 120 will carry the jaws 70 and 72 distally. The guiding arcuate surfaces 116 and 118 of the end cap 110 will engage the arcuate portions 130 and 131 of the jaws to rotate the jaws open. A track 138 in the proximal end of jaw 70 and an opposing track 139 in jaw 72 provide clearance for the distal end 134 of the inner rod 16. The clearance tracks 138 and 139 allow the proximal ends of the jaws to approach each other as the rod 16 is translated distally without interference between the proximal ends of the jaws and the distal end of the inner rod 16.

Figure 9:
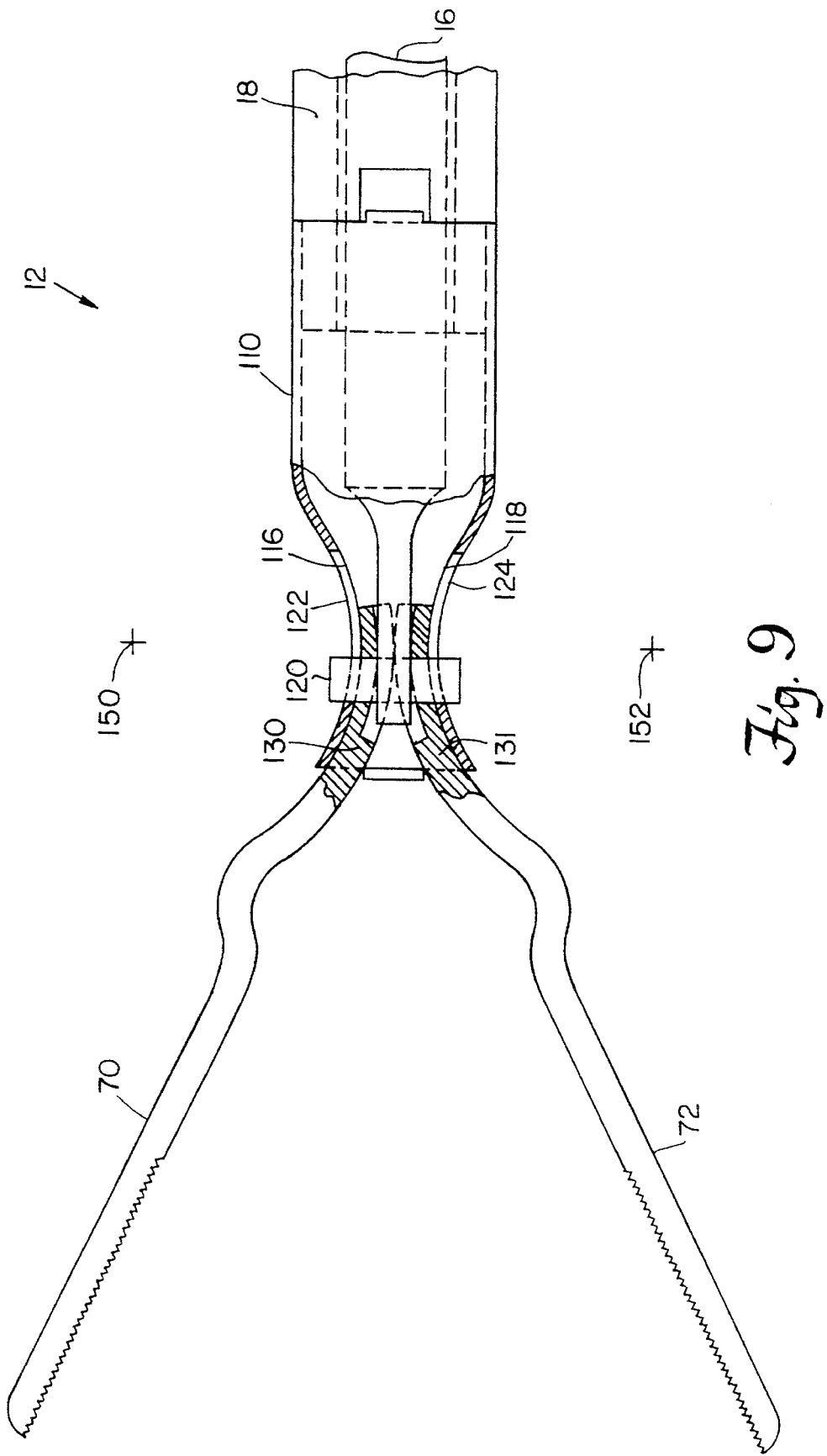
FIG. 9 is a side elevational view of the distal end of the tool assembly of the present invention with the jaws open.

FIG. 9 is a partially cut-away side elevational view of the distal end of the tool assembly 12 with the jaws 70 and 72 in the open position. The inner rod 16 has been translated distally such that the drive pin 120 is at the distal end of slots 122 and 124. The jaws 70 and 72 have been carried forward along with the drive pin 120 such that the arcuate surfaces 116 and 118 and spacing tabs 140 and 141 of the end cap 110 have guided the jaws in rotation to open the jaws 70 and 72.

Each of the arcuate portions 130 and 131 defines an arc having an arc center which is displaced away from the jaw. As mentioned previously, the displacement of the arc center away from the jaw allows for larger arc radii which in turn provide larger opening and closing forces. The arc radius for a jaw of the present invention is preferably between about 0.180 inch and 0.220 inch. The "+" referred to as 150 approximately indicates the center of the arc defined by arcuate portion 130 of jaw 70. The "+" referred to as 152 approximately indicates the center of the arc defined by arcuate portion 131 of jaw 72. As the inner rod 16 is translated, each of the jaws rotates about its respective arc center. That is, jaw 70 rotates about point 150, and jaw 72 rotates about point 152.

FIG. 10 is a cross-sectional view of the distal end of the tool assembly 12 of the present invention. The end cap 110 is attached to the sleeve 18 by tabs 112 and 113 at holes 114 and 115, respectively, on opposite sides of the sleeve 18. Tab 112 of the end cap 110 is bent into hole 114, and tab 113 is bent into hole 115. Drive pin 120 is shown within hole 136 in the distal end 134 of the inner rod 16 and within hole 144 in jaw 70. As the inner rod 16 is translated relative to the outer sleeve 18 and the end cap 110, the drive pin 120 slides along slot 124. Jaw 70 is carried along in the translation. Tabs 140 and 141 on the end cap 110 are also shown. As described above, these tabs keep the jaws 70 and 72 separate during operation and assist in guiding the arcuate portion 130 of jaw 70 along the arcuate surface 116 of the end cap 110.

FIGS. 11a and 11b show top and side views, respectively, of a single jaw 70, 72 of the present invention. The figures depict the hole 144, 146 through which the drive pin 120 passes to carry the jaws 70, 72 back and forth within the end cap 110. Also shown is the clearance track 138, 139 for the distal end 134 of the inner rod 16. The arcuate portion 130, 131 of the jaw is also shown.

FIG. 11b also depicts a slight pitch in the jaw blade 71, 73. In the preferred embodiment, this pitch is approximately 2°. The pitch allows the jaw blades 71, 73 to come together at their extreme distal ends first. This is depicted clearly in FIG. 8. This feature allows the grasper of the present invention to more efficiently grasp small objects. The grasper can easily close on very small objects at the extreme tips of the blades 71, 73. This feature gives the user precise control over the operation being performed.

FIGS. 12a–12k schematically illustrate possible jaw configurations for other embodiments of the invention. Each of the jaw configurations has a distal end 210 having blade portions which open and close. Each jaw configuration also comprises a proximal end 212 which is retained and actuated in accordance with the foregoing detailed description. Each rotating jaw 270, 272 comprises an arc defining portion 230, 231, respectively, each having an arc center 250, 252, respectively. The jaws 270, 272 are translatable relative to a guide member (not shown) which engages the arcuate portions 230, 231 to cause the jaws to rotate about the arc centers 250, 252.

Figure 12A:
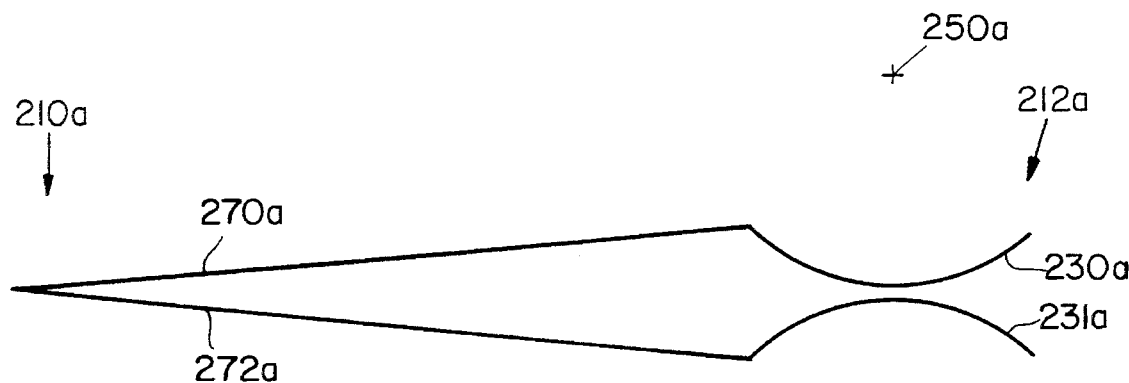
FIGS. 12a–12k are schematic depictions of jaw configurations in accordance with the present invention.
Figure 12B:
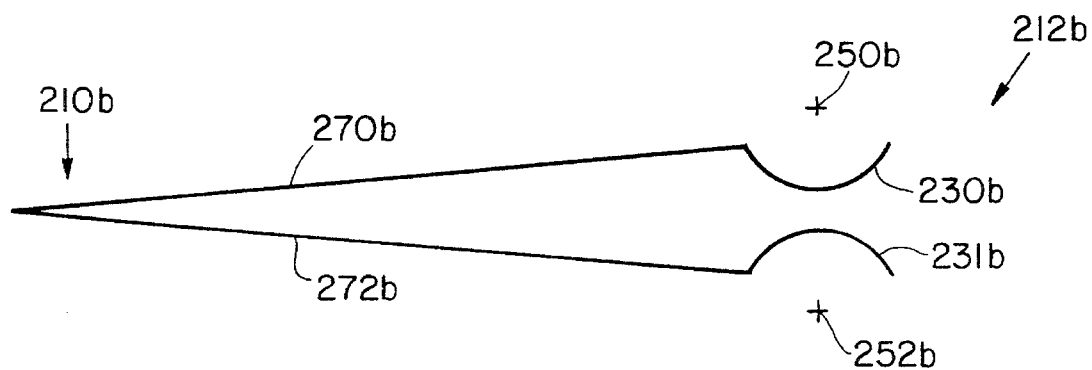

FIGS. 12a and 12b illustrate the jaw configuration of the embodiment described above in detail. The jaws 270, 272 both rotate and are positioned such that the exteriors of their respective arcuate portions face each other. Consequently, the arc centers 250, 252 are located outboard of the jaw configuration.

The main difference between the configurations of FIGS. 12a and 12b is in the radii of the arcs defined by the arcuate portions 230, 231 of the jaws. Arcs 230a and 231a of FIG. 12a have larger radii than the arcs 230b and 231b of FIG. 12b. The result is that for a given amount of longitudinal translation, the jaws of 12a will open and close slower than the jaws of FIG. 12b. The jaws of FIG. 12a will provide a slower, more gradual closing and opening action than will the jaws of FIG. 12b. Consequently, the jaws of FIG. 12a will exhibit a greater closing force than those of FIG. 12b. Thus, the closing force obtainable in a given set of jaws is affected by the radius of the arcuate portions 230 and 231 of the jaws. In FIGS. 12a and 12b, as described in detail above, when the jaws are translated in the proximal direction, they rotate closed. When they are translated distally, they open.

Figure 12C:
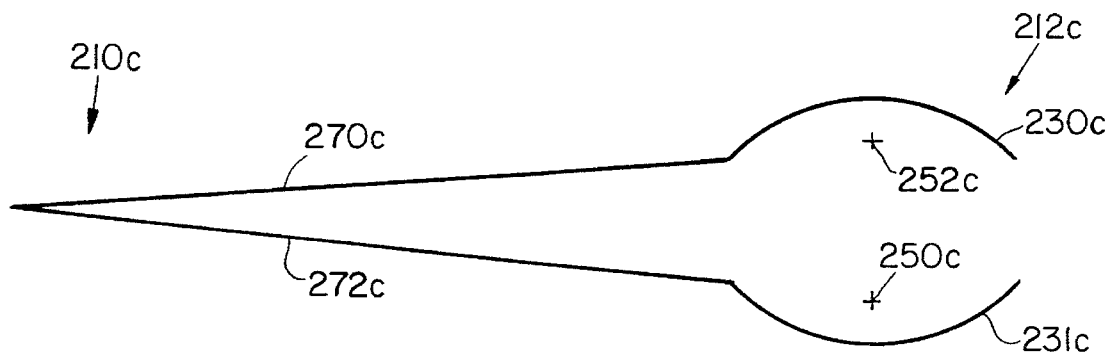
Figure 12D:
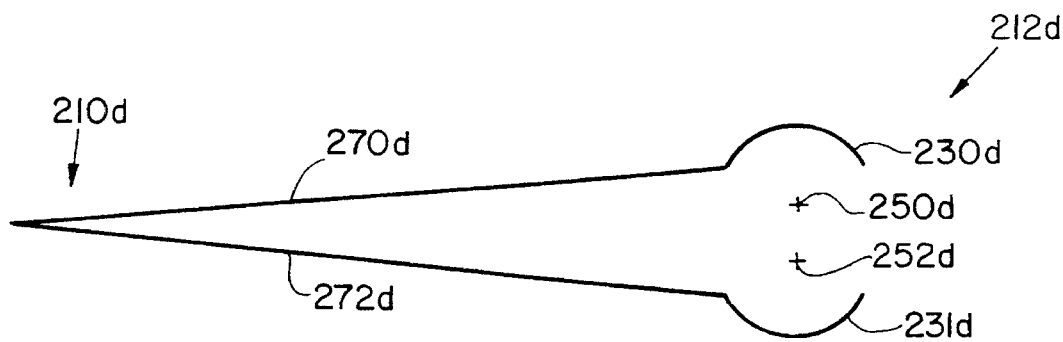
Figure 12E:
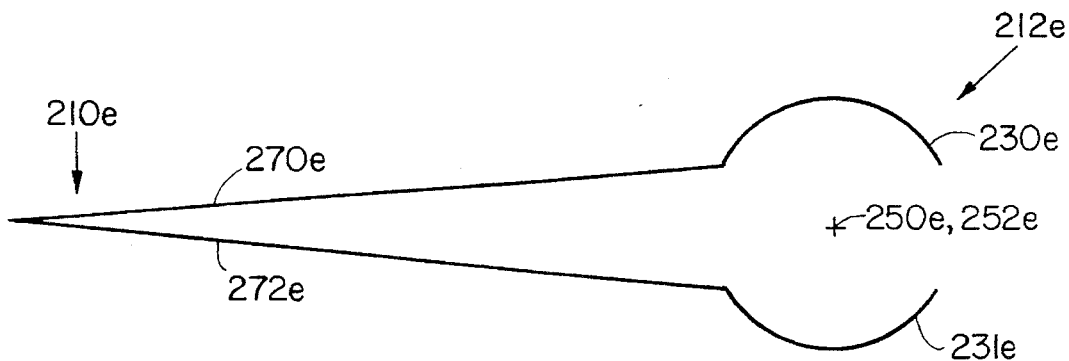

The configurations of FIGS. 12c–12e are similar to those described above, except that the arcuate portions 230 and 231 are oriented such that their interior portions face each other. The jaws of FIGS. 12c–12e are actuated in a manner similar to that described above in connection with the previous embodiments. Longitudinal translation of the jaws along a guide member causes them to rotate about the centers 250 and 252 of their respective arcs 230 and 231. It will be understood that the shape of the guide member must also be different from that described in connection with the previous embodiments. For example, referring to the embodiment described in connection with FIGS. 7–10, the relative orientation of the arcuate surfaces 116 and 118 on end cap 110 would be changed such that the interior portions of their arcs face each other. With that change made, the guide member would then engage the arcuate portions 230, 231 of the jaws to properly rotate them open and closed. The rotational direction for a given translation direction is reversed from that of the previous embodiments. That is, in the embodiments of FIGS. 12c–12e, when the jaws are translated distally, they close. When they are translated proximally, they open.

The feature which distinguishes the embodiments of FIGS. 12c–12e from each other is the radius of the arcuate portions 230, 231 of the rotating jaws 270, 272. Each jaw 270 rotates about the center 250 of its arcuate portion 230, and each jaw 272 rotates about the center 252 of its arcuate portion 231. The jaws of FIG. 12c have comparatively large arc radii. In fact, the radii are so large that the interiors of the arcs overlap. That is, the center 250c of the arc 230c is located between the arc 231c and its center 252c. As with the embodiment of FIG. 12a, this larger arc radius allows for slower gradual opening and closing of the jaws and larger opening and closing forces.

The arcs 230d and 231d of the jaws of FIG. 12d have much smaller radii. The interiors of the arcs no longer overlap. Jaw 270d rotates about arc center 250d, and jaw 272d rotates about arc center 252d. As described above in connection with the embodiment of FIG. 12b, the smaller radii provide for rapid rotational motion for a given longitudinal translation.

In FIG. 12e, the center 250e of arc 230e and the center 252e of arc 231e are located at the same point. The radii of the arcs have been selected such that their centers overlap. Thus, the jaws 270e and 272e rotate about a common point. This need not be accomplished by changing the radius of the arcs. The proximal ends of the jaws may simply be moved closer together or further apart to move the arc centers to the same point. Thus, in the embodiment of FIG. 12c, if the proximal ends of the jaws are moved further apart, arc centers 250c and 252c can be located at the same point. Thus, the benefit of increased closing force can be achieved while the jaws rotate about a common point. In FIG. 12d, the proximal ends of the jaws can be moved closer together to achieve the common point.

Figure 12F:
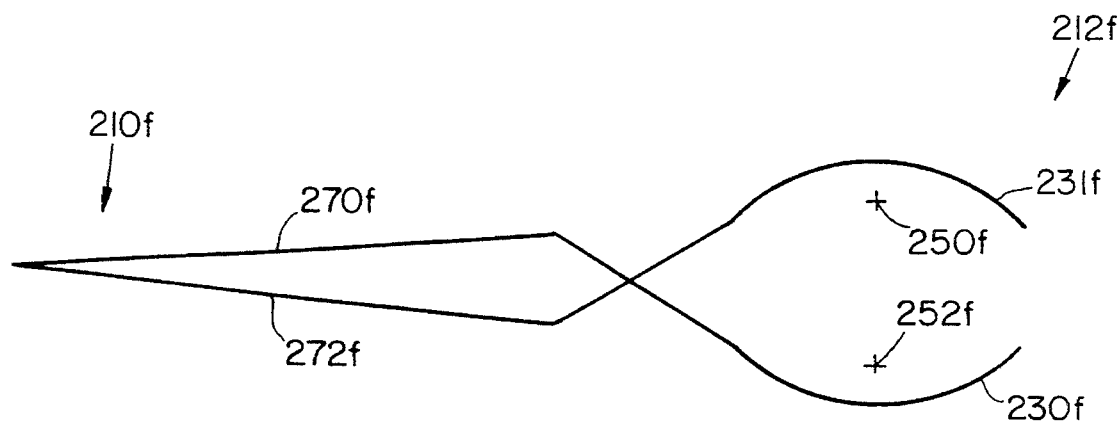
Figure 12G:
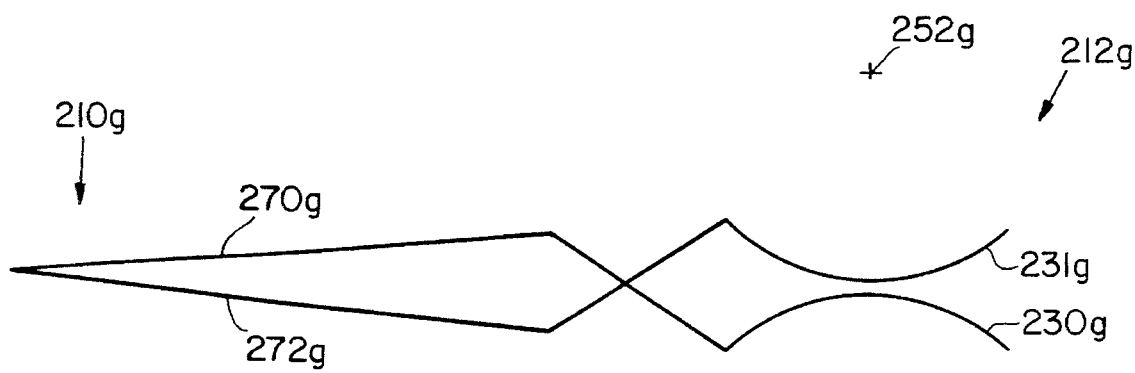

FIGS. 12f and 12g illustrate jaw configurations in which the jaws cross over each other. As with the previous embodiments, jaw 270 rotates about center 250 of its arc 230, and jaw 272 rotates about center 252 of its arc 231. FIG. 12f shows the jaws with the interiors of their arcs facing each other; FIG. 12g shows the interior of the arcs facing away from each other. In FIG. 12f, proximal translation of the jaws along the guide member causes the jaws to close, while distal translation opens them. In FIG. 12g, proximal translation opens the jaws and distal translation closes them.

Figure 12H:
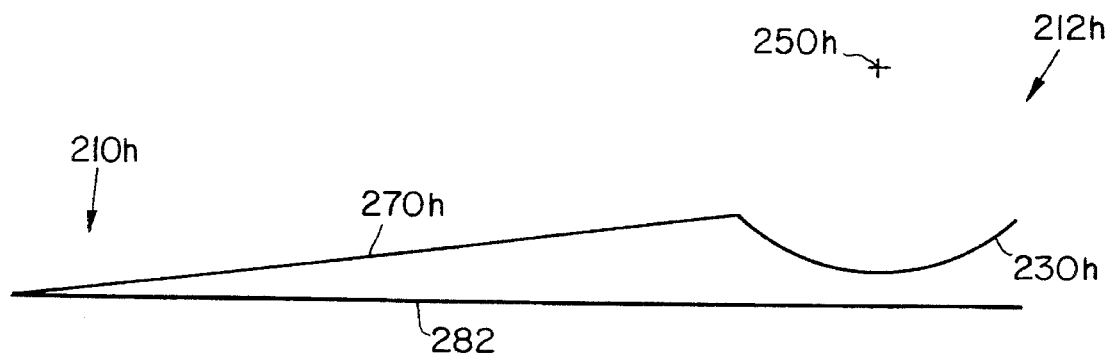
Figure 12I:
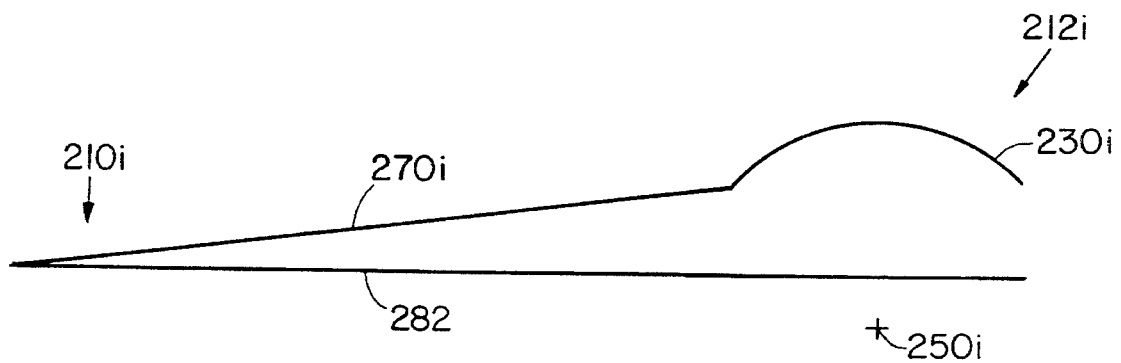

FIGS. 12h and 12i depict jaw configurations in which only one jaw rotates in relation to a stationary jaw or anvil 282. Rotatable jaw 270 rotates about center 250 of arc 230 to open and close against stationary jaw 282. In FIG. 12h, the interior of the arc 230 is directed away from the stationary jaw 282. Proximal translation of the jaw 270h causes it to close against stationary jaw 282. Distal translation causes the jaw 270h to open. In FIG. 12i, the interior of the arc 230 faces the stationary jaw 282. Proximal translation causes the jaw 270i to open; distal translation causes the jaw 270i to close.

Figure 12J:
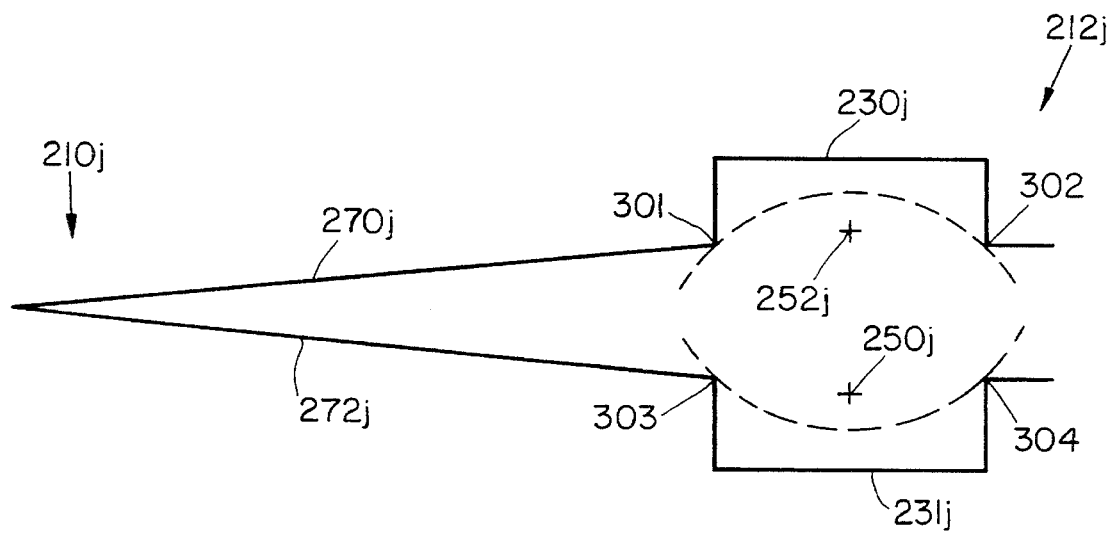
Figure 12K:
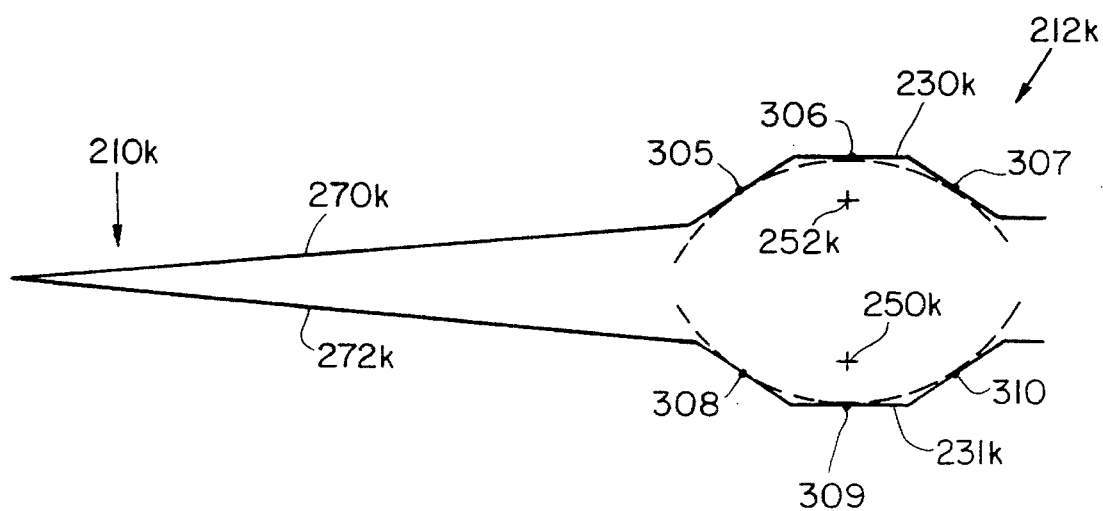

As mentioned previously, the arc defining portions 230, 231 of the jaws 270, 272 need not be arcuate. FIGS. 12j and 12k illustrate two embodiments in which they are not. In FIG. 12j, two points on each arc defining portion define the arc along which the jaw rotates. Points 301 and 302 on jaw 270 define an arc (shown in phantom) whose center is located at 250j. When these points move along an arcuate guide member, the jaw rotates about point 250j. Points 303 and 304 of jaw 272j define the arc whose center is located at 252j. The jaw 272j 1022 rotates about this point 252j when the points 303 and 304 move along an arcuate guide member.

FIG. 12k shows an embodiment in which the arc is defined by three points. Points 305, 306, 307 on jaw 270k define an arc (shown in phantom) centered at 250k. When these points move along an arcuate guide member, the jaw 270k rotates about point 250k. When points 308, 309, 310 of jaw 272k move along an arcuate guide member, the jaw rotates about point 252k.

It will be understood that FIGS. 12j and 12k are only two examples of an infinite number of possible shapes. The present invention contemplates arc defining jaw portions which have a plurality of points which define an arc having a center displaced from the jaw.

Figure 13:
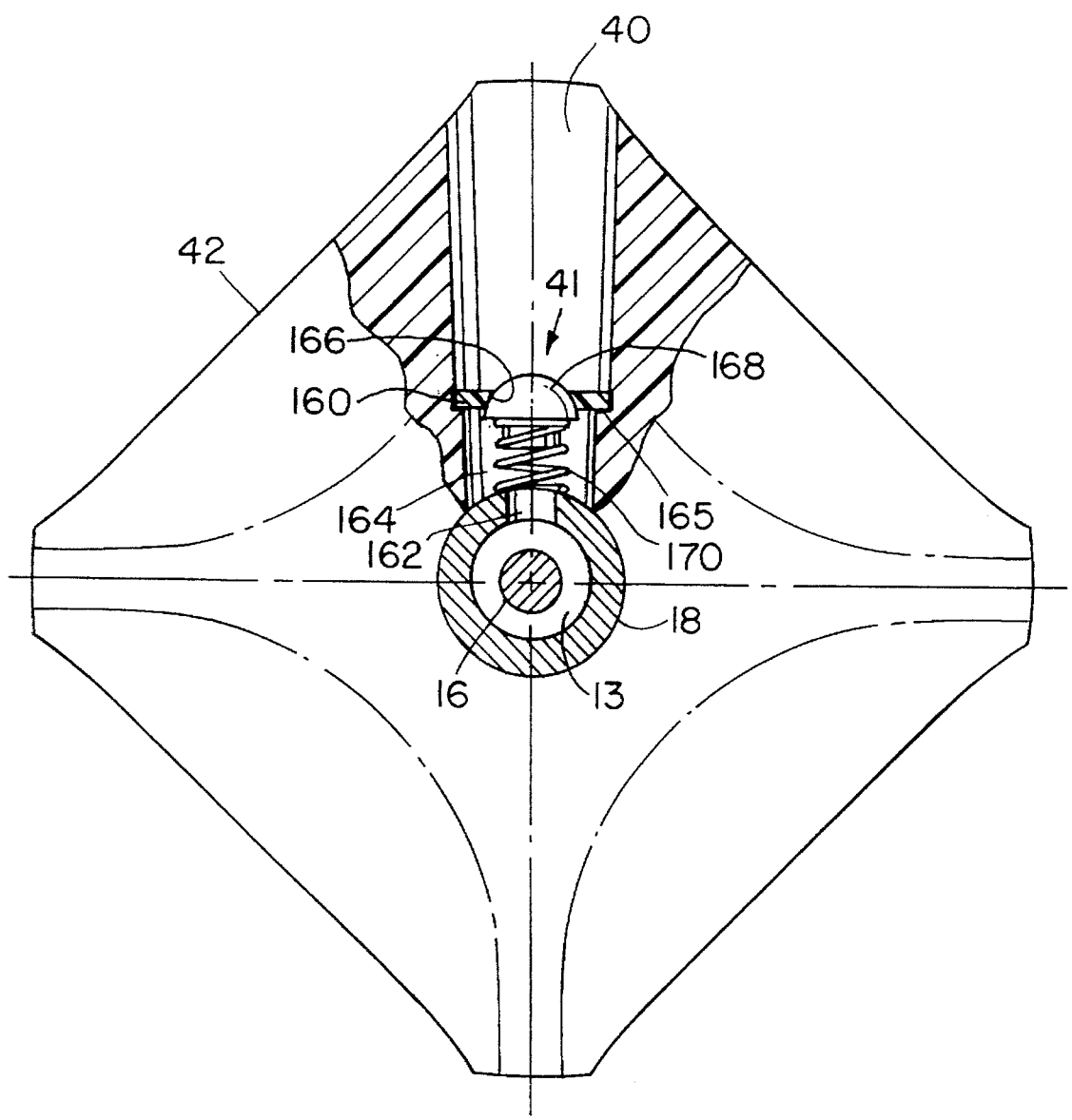
FIG. 13 is a partially cut-away view of the rotating knob of the present invention showing the cleaning port and valve of the present invention.

FIG. 13 details the cleaning port 40 and poppet valve 41 of the present invention. FIG. 13 is a view looking toward the distal end of the tool assembly 12. After use of the surgical instrument 10, it is desirable to clean the inside of sleeve 18 and the inner rod 16. For that purpose, the present invention comprises a port 40 in the rotating knob 42 through which cleaning fluid may be introduced via a syringe (not shown). In the embodiment of the poppet valve shown in FIG. 13, a plastic washer 160 comprises a tapered through hole 166 which serves as a valve seat against the poppet 168. The washer 168 is welded by known means to a shoulder 165. When welded in place, the plastic washer 165 captures the poppet 168 between a coil spring 170 and the valve seat 166 within a chamber 164. The spring 170 rests on the outer diameter of the sleeve 18 and is slightly compressed by the poppet 168 and washer 165 to force the poppet 168 against the valve seat 166. The poppet 168 so biased by the spring 170 prevents fluids within the interior of sleeve 18 from migrating up into the port 40 and out of the instrument 10. At the same time, the poppet 41 allows fluid to be introduced into the interior of sleeve 18 via the port 40. In another embodiment, a ball valve can be used instead of the poppet valve.

To clean the interior of the sleeve 18 and the inner rod 16, a syringe having a luer taper which matches the luer taper of the port 40 is inserted into the port 40. The plunger of the syringe is depressed to introduce fluid into the port 40. The pressure of the cleaning fluid within the port 40 forces the poppet 168 out of the hole 166 against the bias force of the spring 170. With the poppet out of the hole 166, the cleaning fluid passes from port 40 into chamber 164 then through hole 162 and into the interior of sleeve 18. The cleaning fluid then flows through the space 13 between the inner rod 16 and the outer sleeve 18 and out the distal end of the tool assembly 12 near the jaw assembly 66, thus cleaning the tool assembly 12 for the next use.

While this invention has been particularly shown and described with references to preferred embodiments thereof, it will be understood by those skilled in the art that various changes in form and details may be made therein without departing from the spirit and scope of the invention as defined by the appended claims.

The invention claimed is:

1. A surgical instrument comprising:
   a tool assembly comprising:
      an elongate jaw actuation device having a proximal end and a distal end, the jaw actuation device comprising:
         an outer sleeve,
         an inner rod within the outer sleeve, one of the inner rod and the outer sleeve being longitudinally translatable relative to the other, and
         a guide member coupled to the distal end of the jaw actuation device, and
      first and second rotatable jaws, each rotatable jaw comprising an arc defining portion shaped to define an arc having a center which is displaced from the jaw, the rotatable jaws being coupled to the distal end of the jaw actuation device and engaging the guide member at the arc defining portions of the rotatable jaws such that, as one of the inner rod and the outer sleeve is longitudinally translated relative to the other, the arc defining portions of the rotatable jaws move relative to the guide member and are guided by the guide member to rotate each rotatable jaw approximately about the center of its respective arc without changing the shape of the rotatable jaw; and
   a handle assembly for retaining the tool assembly at its proximal end and translating one of the inner rod and the outer sleeve relative to the other to rotate the rotatable jaws.

2. The surgical instrument of claim 1 wherein the arc defining portion of each rotatable jaw is arcuate.

3. The surgical instrument of claim 1 wherein the handle assembly comprises a releasable retainer for retaining the tool assembly such that the tool assembly is detachable from the handle assembly.

4. The surgical instrument of claim 1 wherein the guide member comprises an arcuate portion.

5. The surgical instrument of claim 1 further comprising a ratchet device coupled between the tool assembly and the handle assembly near the proximal end of the tool assembly comprising:
   a ratchet member attached to the handle assembly comprising a plurality of grooves; and
   a shoulder attached to the jaw actuation device engageable with the grooves on the ratchet member, the ratchet member and the shoulder moving relative to each other as one of the inner rod and the outer sleeve is translated relative to the other, the relative motion between the ratchet member and the shoulder causing the shoulder to slide in and out of engagement with the grooves on the ratchet member such that rotating force is providable to the jaw in increments.

6. The surgical instrument of claim 6 wherein the ratchet member is pivotable such that the grooves on the ratchet member can be prevented from engaging the shoulder.

7. The surgical instrument of claim 5 wherein the shoulder is attached to the inner rod.

8. The surgical instrument of claim 1 further comprising a cleaning port in the tool assembly for allowing cleaning fluid into the tool assembly.

9. The surgical instrument of claim 8 wherein the cleaning port comprises a poppet type valve.

10. The surgical instrument of claim 1 wherein the handle assembly further comprises a retainer for retaining the outer sleeve against longitudinal movement relative to the handle.

11. The surgical instrument of claim 1 wherein:
    the inner rod is coupled to the rotatable jaws; and
    the outer sleeve is coupled to the guide member.

12. The surgical instrument of claim 1 further comprising:
    a translation member coupled to the jaw actuation device near the proximal end of the jaw actuation device and engageable by the handle assembly to translate one of the inner rod and the outer sleeve relative to the other; and
    a coupler coupling the translation member to the jaw actuation device, the coupler including a spring for limiting force applied to rotate the jaws.

13. The surgical instrument of claim 12 wherein the translation member is coupled to the inner rod.

14. The surgical instrument of claim 1 wherein the tool assembly further comprises a drive pin engaging the first and second rotatable jaws to move the first and second rotatable jaws relative to the guide member as one of the inner rod and the outer sleeve is translated relative to the other.

15. A surgical tool assembly comprising:
    an elongate jaw actuation device having a proximal end and a distal end, the jaw actuation device comprising:
       an outer sleeve,
       an inner rod within the outer sleeve, one of the inner rod and the outer sleeve being longitudinally translatable relative to the other, and
       a guide member coupled to the distal end of the jaw actuation device;
    first and second rotatable jaws, each rotatable jaw comprising an arc defining portion shaped to define an arc having a center which is displaced from the jaw, the rotatable jaws being coupled to the distal end of the jaw actuation device and engaging the guide member at the arc defining portions of the rotatable jaws such that, as one of the inner rod and the outer sleeve is longitudinally translated relative to the other, the arc defining portions of the rotatable jaws move relative to the guide member and are guided by the guide member to rotate each rotatable jaw approximately about the center of its respective arc without changing the shape of the rotatable jaw.

16. The surgical tool assembly of claim 15 wherein the arc defining portion of each rotatable jaw is arcuate.

17. The surgical tool assembly of claim 15 wherein the guide member comprises an arcuate portion.

18. The surgical tool assembly of claim 15 further comprising:
    a translation member coupled to the jaw actuation device near the proximal end of the jaw actuation device and being engageable to longitudinally translate one of the inner rod and the outer sleeve relative to the other to rotate the jaws; and
    a coupler coupling the translation member to the jaw actuation device, the coupler including a spring for limiting force applied to rotate the jaws.

19. The surgical tool assembly of claim 15 further comprising a shoulder coupled to the jaw actuation device near the proximal end of the jaw actuation device, said shoulder being engageable by a groove to inhibit relative translational motion between one of the inner rod and the outer sleeve.

20. The surgical tool assembly of claim 15 further comprising a cleaning port for allowing cleaning fluid into the tool assembly.

21. The surgical tool assembly of claim 20 wherein the cleaning port comprises a poppet type valve.

22. The surgical tool assembly of claim 15 wherein:
the rotatable jaws are coupled to the inner rod; and
the guide member is coupled to the outer sleeve.

23. The surgical tool assembly of claim 22 wherein the guide member comprises an arcuate portion.

24. The surgical tool assembly of claim 15 further comprising a drive pin engaging the first and second rotatable jaws to move the first and second rotatable jaws relative to the guide member as one of the inner rod and the outer sleeve is translated relative to the other.

25. A jaw for a surgical instrument comprising:
a distal end having a jaw blade; and
a proximal end having a portion which is formed to a shape which defines an arc having a center which is displaced from the jaw, said portion being engageable by a guide member to rotate the jaw approximately about the center of the arc as the jaw and the guide member move relative to each other.

26. The jaw of claim 25 wherein the portion of the proximal end of the jaw which is formed to a shape which defines the arc is arcuate.

27. A method of using an endoscopic surgical instrument comprising:
providing a surgical instrument comprising:
an elongate jaw actuation device having a proximal end and a distal end, the jaw actuation device comprising:
an outer sleeve,
an inner rod within the outer sleeve, one of the inner rod and the outer sleeve being longitudinally translatable relative to the other, and
a guide member coupled to the distal end of the jaw actuation device, and
first and second rotatable jaws, each rotatable jaw comprising an arc defining portion shaped to define an arc having a center which is displaced from the jaw, the rotatable jaws being coupled to the distal end of the jaw actuation device and engaging the guide member at the arc defining portions of the rotatable jaws such that, as one of the inner rod and the outer sleeve is longitudinally translated relative to the other, the arc defining portions of the rotatable jaws moves relative to the guide member and are guided by the guide member to rotate each rotatable jaw approximately about the center of its respective arc without changing the shape of the rotatable jaw, and
a handle assembly for retaining the tool assembly at its proximal end and translating one of the inner rod and the outer sleeve relative to the other to rotate the rotatable jaw; and
with the handle assembly, translating one of the inner rod and the outer sleeve relative to the other to rotate the rotatable jaws.

28. A surgical instrument comprising:
a tool assembly comprising:
an elongate jaw actuation device having a proximal end and a distal end, the jaw actuation device comprising:
an outer sleeve,
an inner rod within the outer sleeve, one of the inner rod and the outer sleeve being longitudinally translatable relative to the other, and
a guide member coupled to the distal end of the jaw actuation device and having an arcuate portion, and
first and second rotatable jaws, each rotatable jaw comprising an arc defining portion shaped to define an arc having a center which is displaced from the jaw, the rotatable jaws being coupled to the distal end of the jaw actuation device and engaging the arcuate portion of the guide member at the arc defining portions of the rotatable jaws such that, as one of the inner rod and the outer sleeve is longitudinally translated relative to the other, the arc defining portions of the rotatable jaws move relative to the guide member and are guided by the guide member to rotate each rotatable jaw approximately about the center of its respective arc; and
a handle assembly for retaining the tool assembly at its proximal end and translating one of the inner rod and the outer sleeve relative to the other to rotate the rotatable jaws.

29. A surgical instrument comprising:
a tool assembly comprising:
an elongate jaw actuation device having a proximal end and a distal end, the jaw actuation device comprising:
an outer sleeve,
an inner rod within the outer sleeve, one of the inner rod and the outer sleeve being longitudinally translatable relative to the other,
a cleaning port for allowing cleaning fluid into the tool assembly, and
a guide member coupled to the distal end of the jaw actuation device, and
first and second rotatable jaws, each rotatable jaw comprising an arc defining portion shaped to define an arc having a center which is displaced from the jaw, the rotatable jaws being coupled to the distal end of the jaw actuation device and engaging the guide member at the arc defining portions of the rotatable jaws such that, as one of the inner rod and the outer sleeve is longitudinally translated relative to the other, the arc defining portions of the rotatable jaws move relative to the guide member and are guided by the guide member to rotate each rotatable jaw approximately about the center of its respective arc; and
a handle assembly for retaining the tool assembly at its proximal end and translating one of the inner rod and the outer sleeve relative to the other to rotate the rotatable jaws.

30. The surgical instrument of claim 29 wherein the cleaning port comprises a poppet type valve.

31. A surgical instrument comprising:
a tool assembly comprising:
an elongate jaw actuation device having a proximal end and a distal end, the jaw actuation device comprising:
an outer sleeve,
an inner rod within the outer sleeve, one of the inner rod and the outer sleeve being longitudinally translatable relative to the other, and
a guide member coupled to the distal end of the jaw actuation device, and
first and second rotatable jaws, each rotatable jaw comprising an arc defining portion shaped to define an arc having a center which is displaced from the jaw, the rotatable jaws being coupled to the distal end of the jaw actuation device and engaging the guide member at the arc defining portions of the rotatable jaws such that, as one of the inner rod and the outer sleeve is longitudinally translated relative to the other, the arc defining portions of the rotatable jaws move relative to the guide member and are guided by the guide member to rotate each rotatable jaw approximately about the center of its respective arc; and a handle assembly comprising a retainer for retaining the tool assembly at its proximal end and retaining the outer sleeve against longitudinal movement relative to the handle assembly, the handle assembly translating the inner rod relative to the outer sleeve to rotate the rotatable jaws.

32. A surgical instrument comprising:

a tool assembly comprising:
  an elongate jaw actuation device having a proximal end and a distal end, the jaw actuation device comprising:
    an outer sleeve,
    an inner rod within the outer sleeve, one of the inner rod and the outer sleeve being longitudinally translatable relative to the other, and
    a guide member coupled to the distal end of the jaw actuation device,
  first and second rotatable jaws, each rotatable jaw comprising an arc defining portion shaped to define an arc having a center which is displaced from the jaw, the rotatable jaws being coupled to the distal end of the jaw actuation device and engaging the guide member at the arc defining portions of the rotatable jaws such that, as one of the inner rod and the outer sleeve is longitudinally translated relative to the other, the arc defining portions of the rotatable jaws move relative to the guide member and are guided by the guide member to rotate each rotatable jaw approximately about the center of its respective arc,
  a translation member coupled to the jaw actuation device near the proximal end of the jaw actuation device and engageable to translate one of the inner rod and the outer sleeve relative to the other, and
  a coupler coupling the translation member to the jaw actuation device, the coupler including a spring for limiting force applied to rotate the rotatable jaws; and a handle assembly for retaining the tool assembly at its proximal end and translating one of the inner rod and the outer sleeve relative to the other to rotate the rotatable jaws.

33. The surgical instrument of claim 32 wherein the translation member is coupled to the inner rod.

34. A surgical instrument comprising:

a tool assembly comprising:
  an elongate jaw actuation device having a proximal end and a distal end, the jaw actuation device comprising:
    an outer sleeve,
    an inner rod within the outer sleeve, one of the inner rod and the outer sleeve being longitudinally translatable relative to the other, and
    a guide member coupled to the distal end of the jaw actuation device;
  at least one rotatable jaw comprising an arc defining portion shaped to define an arc having a center which is displaced from the jaw, the rotatable jaw being coupled to the distal end of the jaw actuation device and engaging the guide member at the arc defining portion of the rotatable jaw such that, as one of the inner rod and the outer sleeve is longitudinally translated relative to the other, the arc defining portion of the rotatable jaw moves relative to the guide member and is guided by the guide member to rotate the rotatable jaw approximately about the center of the arc; and
  a drive pin engaging the rotatable jaw to move the rotatable jaw relative to the guide member to rotate the rotatable jaw as one of the inner rod and outer sleeve is translated relative to the other; and a handle assembly for retaining the tool assembly at its proximal end and translating one of the inner rod and the outer sleeve relative to the other to rotate the rotatable jaw.

* * * * *

UNITED STATES PATENT AND TRADEMARK OFFICE
CERTIFICATE OF CORRECTION

PATENT NO. : 5,499,998
DATED : March 19, 1996
INVENTOR(S) : John C. Meade

It is certified that error appears in the above-indentified patent and that said Letters Patent is hereby corrected as shown below:

In Claim 6, column 15, line 61, delete "claim 6" and insert --claim 5--.

In Claim 27, column 17, line 45, delete the word "moves" and insert --move--; at line 52, delete the word "jaw" and insert --jaws--.

Signed and Sealed this

Ninth Day of July, 1996

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,499,998
DATED      : March 19, 1996
INVENTOR(S): John C. Meade

It is certified that error appears in the above-identified patent and that said Letters Patent is hereby corrected as shown below:

On the title page, item [54],
    In the title, delete "ENDOSCOPTIC" and insert --ENDOSCOPIC--.

Signed and Sealed this

Third Day of March, 1998

Attest:

BRUCE LEHMAN

*Attesting Officer*       Commissioner of Patents and Trademarks